United States Patent [19]

Draber et al.

[11] Patent Number: 4,565,566
[45] Date of Patent: Jan. 21, 1986

[54] IMIDAZO-PYRROLO-PYRIDINE DERIVATIVES USEFUL AS HERBICIDAL AGENTS

[75] Inventors: Wilfried Draber, Wuppertal; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 752,214

[22] Filed: Jul. 3, 1985

[30] Foreign Application Priority Data

Jul. 7, 1984 [DE] Fed. Rep. of Germany ....... 3425124
Jun. 7, 1985 [DE] Fed. Rep. of Germany ....... 3520390

[51] Int. Cl.[4] .................. A01N 43/48; C07D 487/00; C07F 7/02
[52] U.S. Cl. .......................... 71/92; 546/82; 546/14
[58] Field of Search .................. 546/82, 14; 71/92

[56] References Cited

U.S. PATENT DOCUMENTS 4,511,568 4/1985 Bare et al. ................. 546/82

Primary Examiner—Henry R. Jiles
Assistant Examiner—J. Richter
Attorney, Agent, or Firm—Sprung, Horn, Kramer & Woods

[57] ABSTRACT

Novel herbicides of the formula

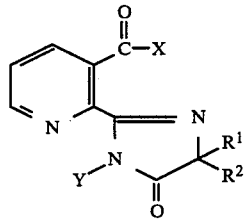

in which
 $R^1$ and $R^2$ each independently is alkyl,
 X is cyano, alkoxycarbonyl or aminocarbonyl, and
 Y is hydrogen or, if X is cyano, may also be trimethylsilyl, can be prepared by reacting an imidazo-pyrrolo-pyridine of the formula

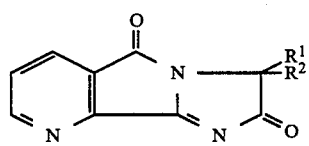

with trimethylsilyl cyanide of the formula

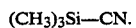

9 Claims, No Drawings

IMIDAZO-PYRROLO-PYRIDINE DERIVATIVES USEFUL AS HERBICIDAL AGENTS

The invention relates to new imidazo-pyrrolo-pyridine derivatives, processes for their preparation and their use as herbicides.

It is already known that certain 2-(2-imidazolin-2-yl)-pyridines, such as, for example, 2-(4,4-dimethyl-5-oxo-2-imidazolin-2-yl)-3-methoxycarbonyl-pyridine, have herbicidal properties (compare, for example, European Published Application 41,623).

However, the herbicidal action of these already known compounds towards harmful plants, as well as their tolerance towards important crop plants, is not always completely satisfactory in all fields of use. New imidazo-pyrrolo-pyridine derivatives of the general formula (I)

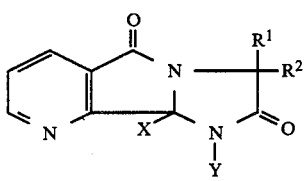

in which
R$^1$ and R$^2$ independently of one another represent alkyl,
X represents cyano, alkoxycarbonyl or aminocarbonyl and
Y represents hydrogen or, if X represents cyano, also the trimethylsilyl group,
have now been found.

It has furthermore been found that the new imidazo-pyrrolo-pyridine derivatives of the formula (I)

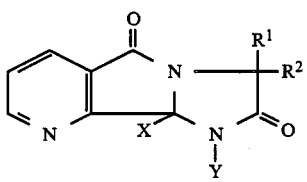

in which
R$^1$ and R$^2$ independently of one another represent alkyl,
X represents cyano, alkoxycarbonyl or aminocarbonyl and
Y represents hydrogen or, if X represents cyano, also the trimethylsilyl group,
are obtained by a process in which
(a) imidazo-pyrrolo-pyridines of the formula (II)

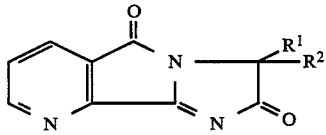

in which
R$^1$ and R$^2$ have the abovementioned meaning, are reacted with trimethylsilyl cyanide of the formula (III)

$$(CH_3)_3Si-CN \quad (III)$$

if appropriate in the presence of a diluent, or in which
(b) the imidazo-pyrrolo-trimethylsilyl-pyridines obtainable by process (a) of the formula (Ia)

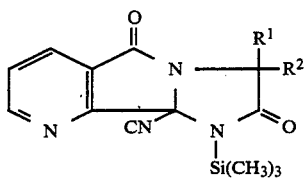

in which
R$^1$ and R$^2$ have the abovementioned meaning, are hydrolysed by reaction with hydroxy compounds of the formula (IV)

$$R^3-OH \quad (IV)$$

in which
R$^3$ represents hydrogen or alkyl, if appropriate in the presence of a diluent and if appropriate in the presence of a catalyst.

Finally, it has been found that the new imidazo-pyrrolo-pyridine derivatives of the formula (I) have herbicidal properties, in particular also selective herbicidal properties.

Surprisingly, the imidazo-pyrrolo-pyridine derivatives of the formula (I) according to the invention exhibit a considerably higher herbicidal potency, coupled with a comparably good tolerance towards useful plants, than the 2-(2-imidazolin-2-yl)-pyridines which are known from the prior art, such as, for example, 2-(4,4-dimethyl-5-oxo-2-imidazolin-2-yl)-3-methoxycarbonyl-pyridine, and which are closely related compounds chemically and from the point of view of their action.

Formula (I) provides a general definition of the imidazo-pyrrolo-pyridine derivatives according to the invention. Preferred compounds of the formula (I) are those in which:
R$^1$ and R$^2$ independently of one another represent straight-chain or branched alkyl with 1 to 8 carbon atoms,
X represents cyano, aminocarbonyl or straight-chain or branched alkoxycarbonyl with 1 to 8 carbon atoms and
Y represents hydrogen or, in the case where X represents cyano, also the trimethylsilyl group.

Particularly preferred compounds of the formula (I) are those in which:
R$^1$ and R$^2$ independently of one another represent methyl, ethyl, n- or i-propyl or n-, i-, s- or t-butyl,
X represents cyano, aminocarbonyl, methoxycarbonyl, ethoxycarbonyl, n- or i-propoxycarbonyl or n-, i-, s- or t-butoxycarbonyl and
Y represents hydrogen or, in the case where X represents cyano, also the trimethylsilyl group.

The compounds of the general formula (I) listed in the preparation examples may be mentioned specifically.

If, for example, the following compounds are used as starting substances, the course of the reaction in process (a) according to the invention can be represented by the following equation:

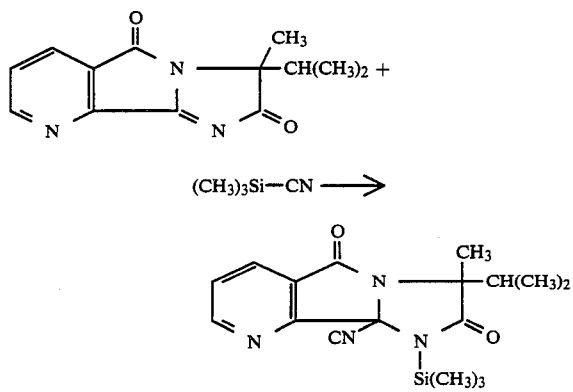

If, for example, the following compounds are used as starting substances, the course of the reaction in process (b) according to the invention can be represented by the following equation:

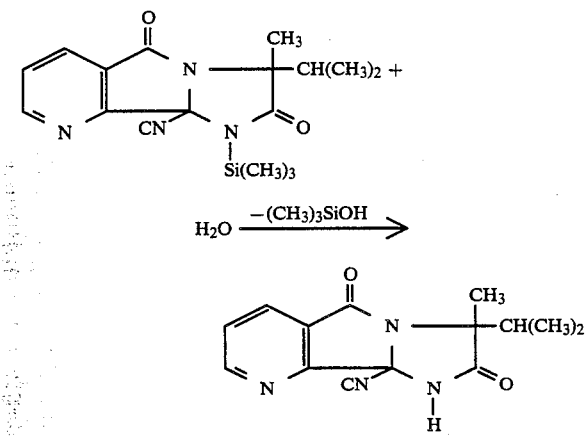

If, for example, the following compounds are used as starting substances and sulphuric acid is used as a catalyst, the course of the reaction in process (b) according to the invention can be represented by the following equation:

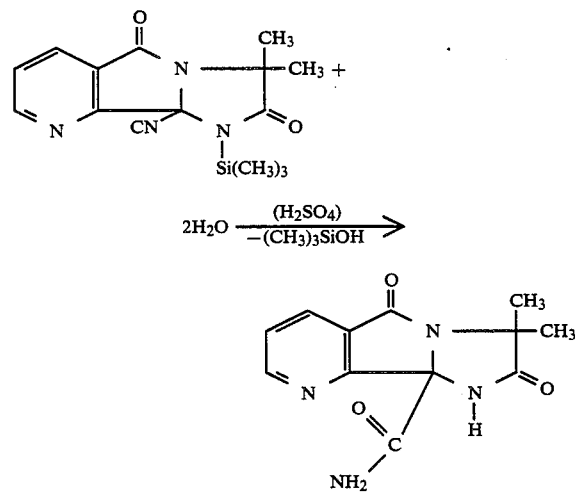

If, for example, the following compounds are used as starting substances and hydrogen chloride is used as a catalyst, the course of the reaction in process (b) according to the invention can be represented by the following equation:

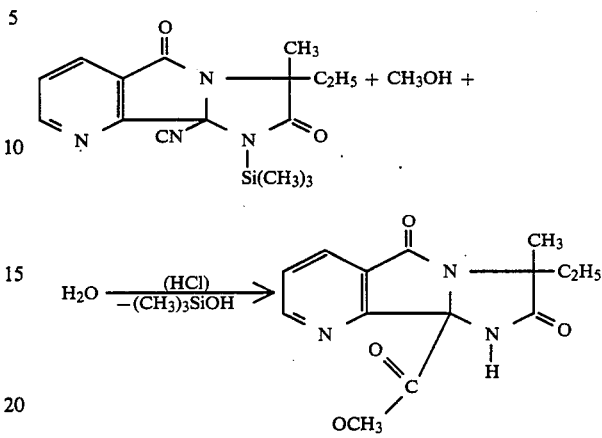

Formula (II) provides a general definition of the imidazo-pyrrolopyridines required as starting substances for carrying out process (a) according to the invention. In this formula (II), $R^1$ and $R^2$ preferably represent those radicals which have already been mentioned as preferred for these substituents in connection with the description of the substances of the formula (I) according to the invention.

The imidazo-pyrrolo-pyridines of the formula (II) and processes for their preparation are known (compare, for example, European Published Application No. 41,623).

The trimethylsilyl cyanide of the formula (III) furthermore required as a starting compound for carrying out process (a) according to the invention is a generally known compound of organic chemistry (compare U.S. Pat. No. 4,328,351).

Formula (Ia) provides a general definition of the imidazo-pyrrolo-trimethylsilyl-pyridines required as starting substances for carrying out process (b) according to the invention. In this formula (Ia) $R^1$ and $R^2$ preferably represent those radicals which have already been mentioned as preferred for these substituents in connection with the description of the substances of the formula (I) according to the invention.

The imidazo-pyrrolo-trimethylsilyl-pyridines of the formula (Ia) are compounds according to the invention and are obtainable by process (a).

Formula (IV) provides a general definition of the hydroxy compounds furthermore required as starting substances for carrying out process (b) according to the invention. In this formula (IV), $R^3$ preferably represents hydrogen or straight-chain or branched alkyl with 1 to 8 carbon atoms, in particular hydrogen, methyl, ethyl, n- or i-propyl or n-, i-, s- or t-butyl.

The hydroxy compounds of the formula (IV) are likewise generally known compounds of organic chemistry.

If appropriate, process (a) according to the invention can be carried out in the presence of a suitable diluent.

Suitable diluents include, in particular, aliphatic or aromatic, optionally halogenated hydrocarbons, such as, for example, gasoline, benzene, toluene, xylene, chlorobenzene, petroleum ether, hexane, cyclohexane, methylene chloride, chloroform and carbon tetrachloride, or ethers, such as diethyl ether, dioxane, tetrahydrofuran or ethylene glycol dimethyl or diethyl ether. An excess of the trimethylsilyl cyanide of the formula (III) used as a reactant is also possible, this simultaneously serving as a diluent.

The reaction temperatures can be varied within a substantial range in carrying out process (a) according to the invention. In general, the reaction is carried out at temperatures between 20° C. and 200° C., preferably at temperatures between 50° C. and 150° C.

For carrying out process (a) according to the invention, in general 1.0 to 30.0 moles, preferably 1.0 to 15.0 moles, of trimethylsilyl cyanide are employed per mole of imidazo-pyrrolo-pyridine of the formula (II).

The reaction mixture is stirred at the required temperature for several hours to days and, to isolate the reaction products of the formula (Ia), is freed from all the volatile constituents in vacuo. The products are characterised and identified by spectroscopic methods, for example by IR or NMR spectroscopy or X-ray analysis.

Process (b) according to the invention can likewise be carried out in the presence of a suitable diluent, if appropriate.

Preferred possible diluents are aliphatic or aromatic, optionally halogenated hydrocarbons, such as, for example, gasoline, benzene, toluene, xylene, chlorobenzene, petroleum ether, naphtha, hexane, cyclohexane, methylene chloride, chloroform or carbon tetrachloride.

However, it is also possible to employ as the diluent a corresponding excess of the hydroxy compounds of the formula (IV) used as the reaction components.

For carrying out process (b) according to the invention, it may be necessary, if appropriate, to add a catalyst. Preferred catalysts which are used are strong inorganic acids, such as sulphuric acid or hydrochloric acid, if appropriate in the presence of a corresponding salt, such as, for example, sodium chloride.

The reaction temperatures can likewise be varied within a substantial range in carrying out process (b) according to the invention. In general, the reaction is carried out at temperatures between 0° C. and 150° C., preferably at temperatures between 20° C. and 100° C.

For carrying out process (b) according to the invention, in general 1.0 to 30.0 moles, preferably 1.0 to 15.0 moles, of hydroxy compounds of the formula (IV) and, if appropriate, 0.1 to 10.0 moles of catalyst acid are employed per mole of imidazo-pyrrolo-trimethylsilyl-pyridine of the formula (Ia).

Depending on the acid strength and concentration and depending on the reaction temperature and the duration of the reaction, either selective splitting off of the trimethylsilyl group or simultaneous hydrolysis of the nitrile function of the compounds of the formula (Ia) is achieved when carrying out process (b) according to the invention. In the case of hydrolysis of the nitrile functions, it is in turn possible, by suitable choice of the reaction conditions (catalyst, temperature and duration of the reaction), to achieve partial hydrolysis to the amide stage or complete hydrolysis to the carboxylic acid stage with simultaneous esterification of the free carboxylic acid group. It is also possible to carry out splitting off of the trimethylsilyl group and subsequent hydrolysis of the nitrile in two separate reaction steps with intermediate isolation of the corresponding compound of the formula (Ib).

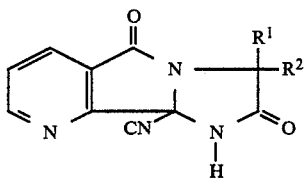

The particular end products of the formula (I) are worked up and isolated by generally customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

*Dicotyledon weeds of the genera*: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

*Dicotyledon cultures of the genera*: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

*Monocotyledon weeds of the genera*: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

*Monocotyledon cultures of the genera*: Oryza, Zea, Triticum, Hordeum, Avena, Secale, Sorghum, Panicum, Saccharum, Ananas, Asparagus and Allium, However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used with particularly good success here for selective pre-emergence and post-emergence combating of monocotyledon and dicotyledon weeds in important crops, preferably dicotyledon crops, such as, for example, cotton or soya bean.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soya bean.

Mixtures with further triazinones or ureas and also diphenyl ethers, such as, for example, 5-(2-chloro-4-trifluoromethylphenoxy)-2-nitro-benzoic acid or -N-methyl-sulphonylbenzamide, methyl 5-(2,4-dichlorophenoxy)-2-nitrobenzoate or 2-benzyloxyethyl or trimethylsilylmethyl 2-[4-(3,5-dichloropyrid-2-yloxy)-phenoxy]-propionate, or cyclohexanediones, such as, for example, 2-[(1-ethoxamino)-butylidene]-5-(2-ethylthiopropyl)-1,3-cyclohexanedione or methyl-6,6-dimethyl-2,4-dioxo-3-[1-(2-propenyloxyamino)-butylidene]-cyclohexanecarboxylic acid, or benzothiadiazinones, such as, for example, 3-isopropyl-2,1,3-benzothiadiazin-4-one 2,2-dioxide, are also possible. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.05 and 10 kg of active compound per hectare of soil surface, preferably between 0.1 and 5 kg per ha.

The preparation and use of the active compounds according to the invention can be seen from the following examples.

PREPARATION EXAMPLES

Example 1

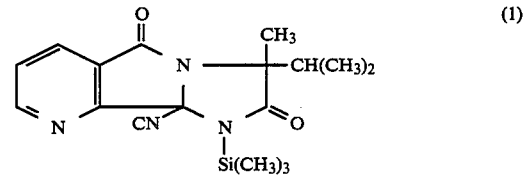

(1)

A mixture of 24.3 g (0.1 mole) of 3-isopropyl-3-methyl-5H-imidazo-[1',2':1,2]pyrrolo[3,4-b]-pyridine-2-(3H),5-dione and 100 ml (79 g, about 1 mole) of trimethylsilyl cyanide is stirred at a bath temperature of 100° C. for 16 hours, cooled and concentrated and the volatile constituents are removed under a high vacuum. 34 g (100% of theory) of compound of Example 1 are obtained as an oil.

NMR (60 MHz; ppm/TMS as an internal standard): 9H, 0.32 (Si(CH$_3$)$_3$); 11H, 0.55, 0.12, 1.5, 2.0 (CH$_3$ and CH(CH$_3$)$_2$); and 3H, 7.5, 8.1, 8.9 (pyridine protons). MS (chemical ionisation with NH$_3$): 343 (M+I), 299 (M+2—CH(CH$_3$)$_2$), 299 (M+I—CH(CH$_3$)$_2$—CN).

NMR=nuclear magnetic resonance spectrum (TMS=tetramethylsilane, (CH₃)₄Si));
MS=mass spectrum (M=molecule ion).

Example 2

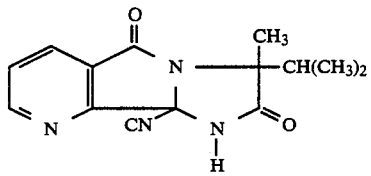
(2)

34.2 g (0.1 mole) of the compound of Example 1, 400 ml of naphtha, 100 ml of methylene chloride and 2.5 ml (0.14 mole) of water are stirred at room temperature (20° C. to 25° C.) for 12 to 15 hours, the mixture is filtered, the filtrate is evaporated and the residue is triturated with ether and filtered off with suction. 22.5 g (83% of theory) of compound of Example 2 of melting point 155° C. (decomposition) are obtained.

Example 3

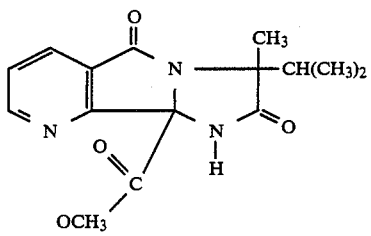
(3)

20.2 g (0.075 mole) of the compound of Example 2, 200 ml of methylene chloride, 12 g (0.375 mole) of methanol and 40 ml of concentrated hydrochloric acid are boiled under reflux for 24 hours, the mixture is cooled and concentrated in vacuo, the residue is taken up in ethyl acetate and the mixture is washed with water and aqueous sodium bicarbonate solution, dried over sodium sulphate and concentrated in vacuo. The oil which remains is chromatographed over a silica gel column (eluant:chloroform/ethyl acetate/methanol—10:10:2). 6.4 g (28% of theory) of compound of Example 3 of melting point 196° C. are obtained.

Example 4

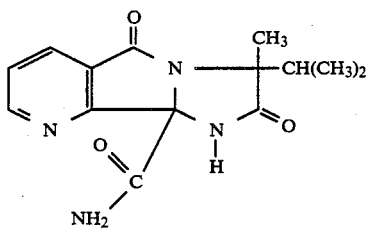
(4)

8.1 g (0.03 mole) of the compound of Example 2, 6 g (0.06 mole) of concentrated sulphuric acid, 1 ml (0.055 mole) of water and 0.17 g (0.003 mole) of sodium chloride are stirred at 40° C. to 50° C. for 4 hours. Thereafter, 50 ml of methanol are added and the mixture is stirred at 50° C. for a further 3 hours and at room temperature (20° C. to 25° C.) for 12 hours. For working up, the mixture is diluted with 50 ml of water and neutralised with sodium bicarbonate and the solid which has precipitated is filtered off with suction and dried. 3.2 g (37% of theory) of compound of Example 4 of melting point 281° C. (decomposition) are obtained.

The compounds of the general formula (I)

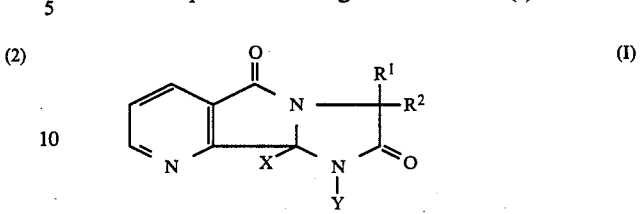
(I)

which are listed below were also obtained in a corresponding manner:

|  | melting point: |
|---|---|
| Example 5: 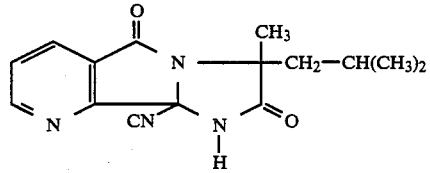 | mp: 176° C. |
| Example 6: 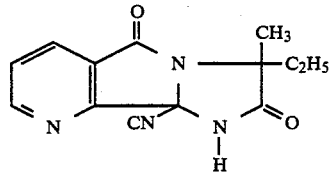 | mp: 167° C. |
| Example 7: 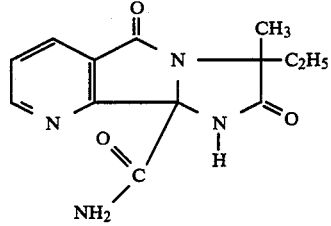 | mp: 295° C. |
| Example 8: 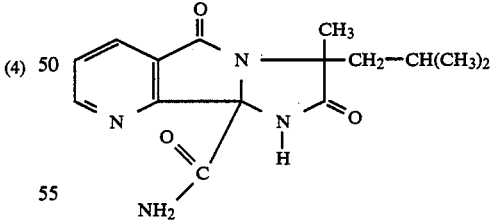 | mp: 265° C. |
| Example 9: 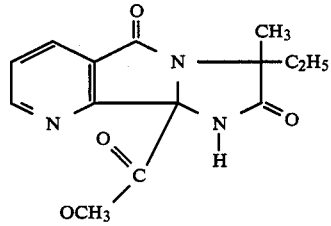 | mp: 160° C. |
| Example 10: | mp: 226° C. |

-continued

| | melting point: |
|---|---|
| 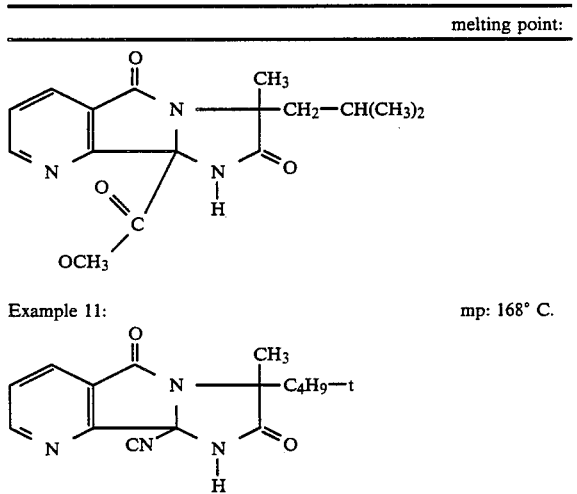 | |
| Example 11: | mp: 168° C. |

Use Examples

The compound shown below was used as a comparison substance in the use examples which follow:

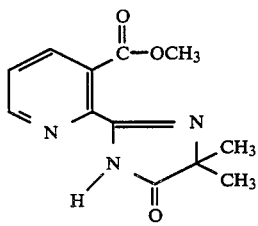

2-(4,4-Dimethyl-5-oxo-2-imidazolin-2-yl)-3-methoxycarbonyl-pyridine (known from European Published Application 41,623)

EXAMPLE A

Pre-emergence test
Solvent: 5 parts by weight of acetone
Emulsifier: 1 part by weight of alkylaryl polyglycol ether To produce a suitable preparation of active compound, 1 part of weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compound according to preparation example 3.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 of water/ha. After three weeks, the degree of damage to the plants is rated in % damage in comparison to the development of the untreated control. The figures denote:

0% = no action (like untreated control)
100% = total destruction

In this test, a clearly superior activity compared with the prior art is shown, for example, by the compounds according to preparation examples 1 and 2.

It will be understood that the specification and examples are illustrative but not limitative of the present invention and that other embodiments within the spirit and scope of the invention will suggest themselves to those skilled in the art.

We claim:

1. An imidazo-pyrrolo-pyridine derivative of the formula

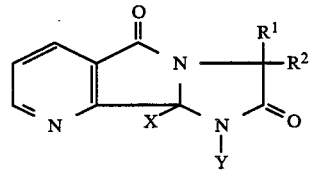

in which
$R^1$ and $R^2$ each independently is alkyl with $C_1$-$C_8$ carbon atom,
X is cyano, alkoxycarbonyl with $C_1$-$C_8$ carbon atoms or aminocarbonyl, and
Y is hydrogen or, if X is cyano, may also be trimethylsilyl.

2. A compound according to claim 1,
in which
$R^1$ and $R^2$ each independently is methyl, ethyl, n- or i-propyl or n-, i-, s- or t-butyl, and
X is cyano, aminocarbonyl, methoxycarbonyl, ethoxycarbonyl, n- or i-propoxycarbonyl or n-, i-, s- or t-butoxycarbonyl.

3. A compound according to claim 1, wherein such compound is of the formula

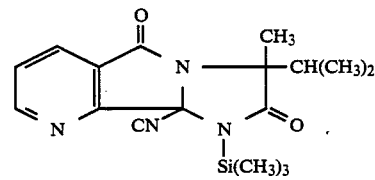

4. A compound according to claim 1, wherein such compound is of the formula

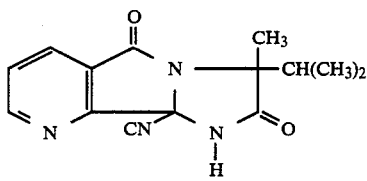

5. A compound according to claim 1, wherein such compound is of the formula

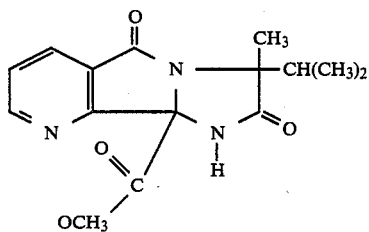

6. A compound according to claim 1, wherein such compound is of the formula

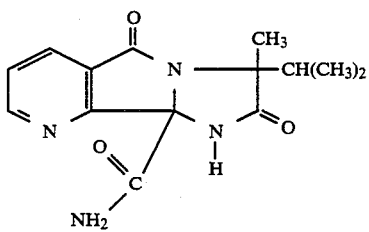

7. A herbicidal composition comprising a herbicidally effective amount of a compound according to claim 1 in admixture with a diluent.

8. A method of combating unwanted vegetation which comprises applying to such vegetation or to a locus from which it is desired to exclude such vegetation a herbicidally effective amount of a compound according to claim 1.

9. The method according to claim 8, wherein such compound is of the formula

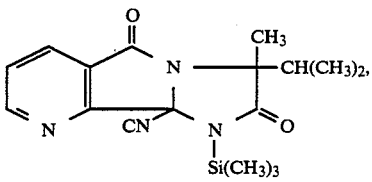

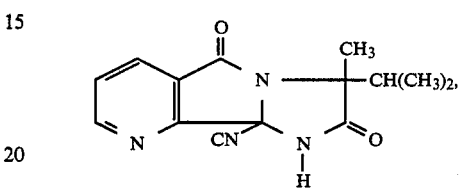

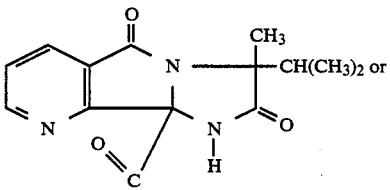

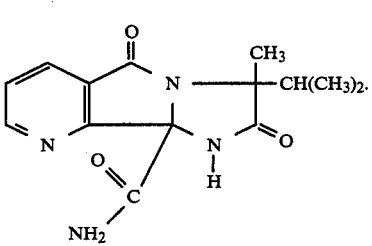

* * * * *